(12) United States Patent
Panicali et al.

(10) Patent No.: US 6,699,475 B1
(45) Date of Patent: Mar. 2, 2004

(54) RECOMBINANT POX VIRUS FOR IMMUNIZATION AGAINST TUMOR-ASSOCIATED ANTIGENS

(75) Inventors: Dennis L. Panicali, Acton, MA (US); René Bernards, Brookline, MA (US)

(73) Assignees: Therion Biologics Corporation, Cambridge, MA (US); Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 08/481,804

(22) Filed: Jun. 7, 1995

Related U.S. Application Data

(62) Division of application No. 07/579,269, filed on Sep. 5, 1990, now abandoned, which is a continuation of application No. 07/092,036, filed on Sep. 2, 1987, now abandoned.

(51) Int. Cl.$^7$ ............................................. A61K 39/12
(52) U.S. Cl. ................................. 424/199.1; 424/232.1; 435/320.1; 435/344.1
(58) Field of Search .................. 424/199.1, 174.1, 424/184.1, 232.1, 277.1; 435/320.1, 344.1, 23, 57, 65; 530/350

(56) References Cited

U.S. PATENT DOCUMENTS

| | | | |
|---|---|---|---|
| 4,603,112 A | | 7/1986 | Paoletti et al. |
| 5,156,841 A | * | 10/1992 | Rapp ........................... 424/88 |
| 5,833,975 A | * | 11/1998 | Paoletti et al. .............. 424/93.2 |
| 6,165,460 A | * | 12/2000 | Schlom et al. ............. 424/93.2 |

FOREIGN PATENT DOCUMENTS

| | | |
|---|---|---|
| GB | 2188637 A | 7/1987 |

OTHER PUBLICATIONS

Davis (1990) Microbiology 3rd Edition, Harper & Row, pp. 540–542, 1236–1236, and 1259.
Mansour et al. (1985) Proc. National Academy of Science 82; 1356–63.
Lathe et al., (Apr. 30, 1987) Nature 326; 878–80.
Kornbluth et al., (1986) Mol. & Cell. Biol. 6(5) 1545–51.
Yamamoto et al., *Nature*, 319: 230–234 (1986).
Martin–Zanca D., et al., *Nature*, 319: 743–748 (Feb. 27, 1986).
Nagarajan, J., et al., *Proc. Natl. Acad. Sci. USA*, 83: 6568–6572 (1986).
Mackett, M. and G. L. Smith, J. Gen. Virol., 67: 2067–2082 (1986).
Yarden, Y. et al., *EMBO J.*, 6: 3341–3351 (1987).
Bernards, R., et al., *Proc. Natl. Acad. Sci.*, 84: 6854–6558 (1987).
Allen, P.M. et al., (1985) *J. Immural* 135: 368–373.
Lathe, R. et al., (1987) *Nature* 326: 878–880.
Padhy, L.C., et al. (1982) Cell 28: 865–871.
Bargmann, et al., *Nature 319*: 226–230.
Panicali, D., et al. *Gene 47*: 193–199 (1986).
Hearing, V.J., et al., *J. Immunol.* 137–379 (1986).
Takahashi and Cooper, *Molecular and Cellular Biology*, 7: 1378–1385 (1987).
Slamon et al., *Science*, 235: 177–182 (1987).
Besmer et al., *Nature*, 320: 415–421 (1986).
Kolata, *Science*, 235: 160–161 (1987).
Paxton, et al., *Proccedings of the NAtional Academy of Sciences, USA.* 84: 920–924 (1987).
Martin–Zanca et al., *Cold Spring HArbor Symposia on Quantitive Biology*, vol. Ll, 1986 Cold Spring Harbor Laboratory, pp. 983–992.
Kraus et al., *EMBO Journal*, 6:605–610 (1987).
Van De Vijver et al., *Molecular and Cellular Biology*, 7:2019–2023 (1987).
Yokota et al., *Lancet* 765–767 (1986).
Mackett, M. and G.L. Smith, J. Gen. Virol., 67: 2067–2082 (1986).
Yarden, Y. et al., EMBO J., 6: 3341–3351 (1987).
Bernards, R., et al., *Proc. Natl. Acad. Sci.,* 84:6854–6858 (1987).

\* cited by examiner

*Primary Examiner*—Ali R. Salimi
(74) *Attorney, Agent, or Firm*—Nixon Peabody LLP

(57) ABSTRACT

Recombinant pox viruses capable of expressing cell-encoded, tumor-associated antigens are disclosed. The recombinant viruses are useful for evoking an immune response against the antigen.

7 Claims, 3 Drawing Sheets

RECOMBINANT POX VIRUS FOR IMMUNIZATION AGAINST TUMOR-ASSOCIATED ANTIGENS

This application is a divisional application of 07/579,269 filed Sep. 5, 1990, now abandoned, which is a continuation application of Ser. No. 07/092,036 filed Sep. 2, 1987, now abandoned.

BACKGROUND

The discovery over the past decade of cellular ocogenes has provided one explanation of the molecular mechanisms that are responsible for the neoplastic conversion of many types of cells.

Nevertheless, these genes and similarly acting cellular elements can at best explain only part of the process of tumor formation. Before growing out into a tumor, the transformed cells must confront and evade physiological mechanisms that are designed to defend the host against cancer.

Prominent in these defenses, presumably are immune mechanisms that involve specific recognition and elimination of tumor cells. These mechanisms are poorly understood: the nature and importance of immunological effector mechanisms are unclear, and the identity of tumor cell markers that may be recognized by these effectors remains mostly elusive.

A desirable mode of cancer treatment is to enlist natural immune mechanisms to establish anti-tumor immunity. Methods for inducing effective anti-tumor immunity, however, remain to be elucidated. One possible way of inducing immune response against a tumor might be to immunize with a tumor-associated antigen. For examples, the ectodomain of the neu-encoded rat p185 protein constitutes a highly immunogenic determinant in tumor-bearing NFS mice which invariably mount a strong serum response to this protein. See, Padhy, L. C. et al. (1982) *Cell*, 28:865–871. Tumors formed from neu-trans-fectants (cells transformed with the neu gene) initially grow rapidly but ultimately are seen to regress. This regression is not seen with tumors formed from other types of oncogene-transfected cells and can be attributed at least partially to recognition of the neu-transfectants by the host immune system. The nature of the immune mechanisms that effect this regression and establish anti-tumor immunity is unclear. It is possible that the p185 antigen alone suffices to induce the anti-tumor response. Alternatively, this antigen may only provoke an effective response when acting in concert with other unrelated, transformation-specific antigens displayed by the oncogene-transformed cells.

A purified, murine melanoma tumor-specific antigen has been demonstrated to elicit tumor rejection of a melanoma. Hearing, V. J. et al. J. *Immunol.*, 137:379 (1986). This work suggests that tumor-associated antigens can be used successfully as targets for tumor immunotherapy. Recently, Lathe et al. showed that immunization of mice with a recombinant vaccinia virus capable of expressing a polyoma-virus encoded antigen induced rejection of viral-induced tumor. Lathe et al. (1987) *Nature* 326, 878–880. The polyoma viral antigen, however, is a completely foreign and highly immunogenic antigen.

SUMMARY OF THE INVENTION

This invention pertains to recombinant pox viruses capable of expressing cell-encoded tumor-associated antigens, to methods of producing the recombinant pox virus, to intermediate DNA vectors which recombine with pox virus in vivo to produce the modified pox viruses and to methods of immunizing a host with the recombinant pox virus to elicit an immune response against a cell-encoded tumor-associated antigen. The invention is based, in part, on the discovery that immunization with the neu antigen via a recombinant pox virus serves as effective prophylaxis against tumors formed by neu oncogene-transfected cells.

Recombinant pox virus capable of expressing a cell-encoded tumor-associated antigen are produced by integrating into the pox virus genome sequences encoding the antigen or immunogenic portions thereof. Tumor-associated antigens can be cellular oncogene-encoded products or aberrantly expressed proto-oncogene-encoded products (e.g. products encoded by the neu, ros, trk, and kit genes) and mutated forms of growth factor receptor or receptor-like cell surface molecules (e.g. surface receptor encoded by the c-erb B gene). Other tumor-associated antigens include molecules which may or may not be directly involved in transformation events, but are expressed by tumor cells (e.g. carcinoembryonic antigen, CA-125, melonoma associated antigens, etc.) In some embodiments the sequence encoding the tumor-associated antigen is engineered to encode a product which retains at least an immunogenic domain but is disabled with respect to its oncogenic activity. For example, truncated products may be designed which contain the immunogenic domains of the natural gene product but which either lack or contain inactivated oncogenic regions.

The DNA sequence encoding the tumor-associated antigen is inserted into a region of the pox virus genome which is nonessential for replication of the pox virus, generally in association with a pox virus promoter to direct its expression.

The DNA-sequence encoding the tumor-associated antigen is integrated into the pox viral genome by an in vivo recombination event between an intermediate DNA vector carrying the DNA encoding the tumor-associated antigen and a pox virus. In essence, the intermediate DNA vector contains the antigen-encoding sequence linked to a pox viral promoter located within a DNA sequence homologous to a region of the pox viral genome which is nonessential for replication of the pox virus. Thus, at minimum the vector comprises:

a. a prokaryotic origin of replication;

b. a pox viral promoter;

c. a sequence encoding a tumor-associated antigen under the direction of the pox viral promoter; and d. DNA sequences of the pox virus into which the gene encoding the antigen sequence is to be integrated, the DNA sequences flanking the promoter and structural gene at both the 5' and 3' end, the DNA sequence being homologous to the region of the pox virus genome where the sequence of the tumor associated antigen is to be inserted.

Recombination of the DNA vector and the pox virus is achieved in an appropriate host cell. Appropriate host cells for in vivo recombination are eukaryotic cells which are 1) transfectable by the DNA vector and 2) infectable by pox virus. The host cell is transfected with the DNA vector carrying the antigen sequence and then infected with the pox virus. The virus is allowed to replicate in the host cell during which time recombination occurs in vivo between the DNA vector and the virus resulting in insertion of the sequence encoding the tumor-associated antigen into the pox virus genome. The recombinant viral progeny is isolated from the wild type virus.

An assayable marker can be co-integrated with the antigen-encoding sequence. Expression of the marker provides a basis for selection of recombinant virus containing integrated DNA. Other methods of selection include detection of the integrated sequences by hybridization with homologous DNA probes. Negative selection procedures can also be used such as selection for absence of the product of the viral gene into which the DNA segment has been inserted. When an assayable marker is located at the viral insertion site, recombinants can be identified by loss of the marker.

The recombinant virus is a virus which expresses in an inoculated host the cellular tumor-associated antigen. The virally-expressed product will trigger cell-mediated and/or humoral immunity against the antigen and cells bearing the antigen.

DETAILED DESCRIPTION OF THE INVENTION

Figure 1:
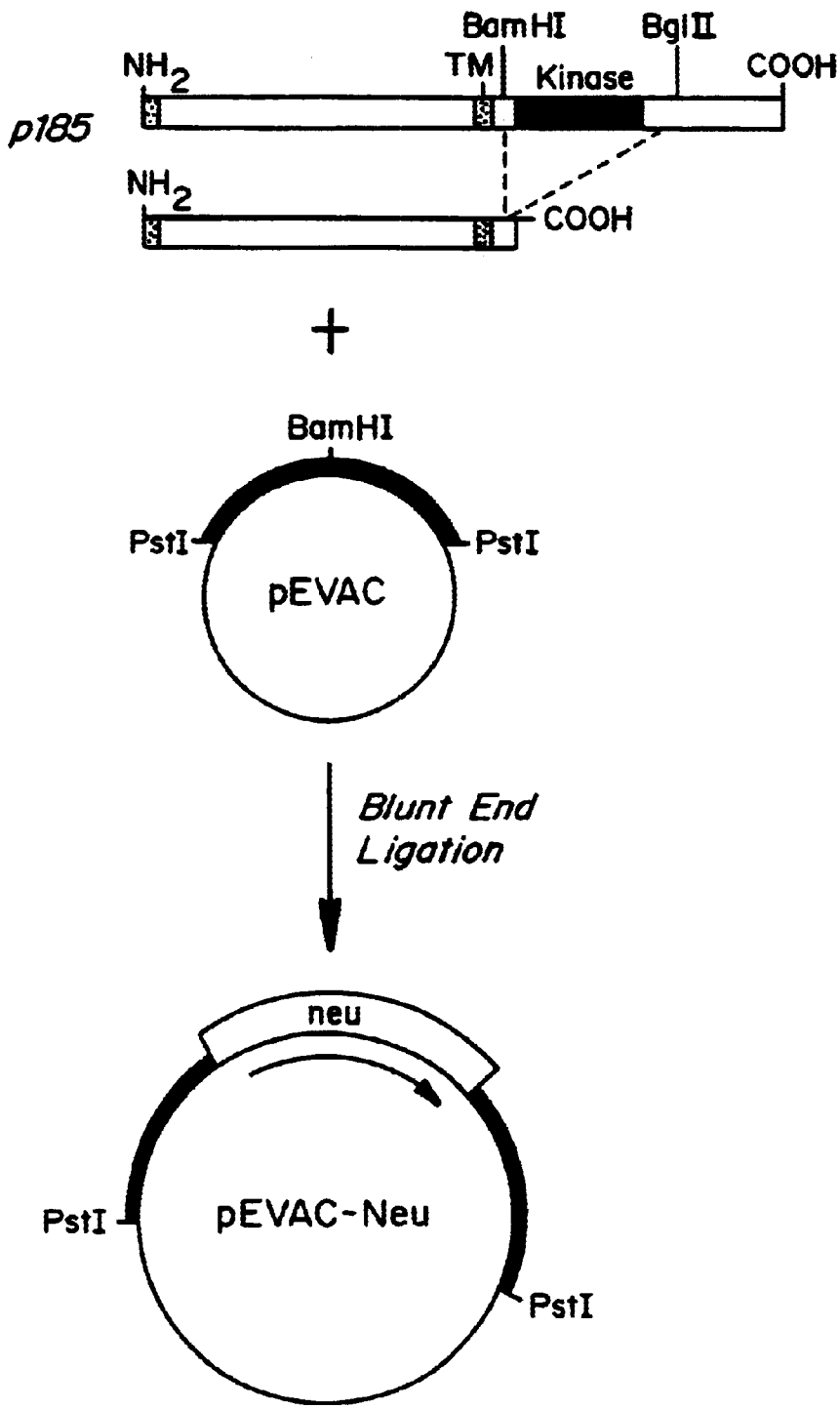
FIG. 1 is a schematic representation of the construction of the pEVAC-neu plasmid.

1. Selection of DNA Sequences Encoding Tumor Associated Antigens.

Pox viruses serve as effective vectors for inducing immunity against tumor-associated antigens. According to this invention, the antigens can be cell-encoded molecules i.e., molecules which are encoded by genes intrinsic to cells as opposed to those encoded by genes introduced by an extrinsic transforming agent such as a virus.

Particularly preferred tumor-associated antigens are cell surface molecules. These are positioned for recognition by elements of the immune systems and thus are excellent targets for immunotherapy.

Genes which encode cellular tumor-associated antigens include cellular oncogenes and proto-oncogenes which are aberrantly expressed. In general, cellular oncogenes encode products which are directly relevant to the transformation of the cell and, because of this, they are particularly preferred targets for immunotherapy. An example is the tumorigenic neu gene which encodes a cell surface molecule which appears to be directly related to the transformation of a cell. Other examples include the ros, kit, and trk genes. The products of proto-oncogenes (the normal genes which are mutated to form oncogenes) can be aberrantly expressed (e.g. overexpressed) and this aberrant expression can be related to cell transformation. Thus, the product encoded by proto-oncogenes can be targeted for immune therapy.

Some oncogenes have been found to encode growth factor receptor molecules or growth factor receptor-like molecules which are expressed on the tumor cell surface. An example is the cell surface receptor encoded by the c-erbB gene. These are particularly suitable for the purpose of this invention.

Other tumor-associated antigens may or may not be directly involved in transformation. These antigens, however, are expressed by certain tumor cells and provide effective targets for immunotherapy. Some examples are carcinoembryonic antigen (CEA), CA 125 (associated with ovarian carcinoma), and melanoma specific antigens.

When a tumor-associated antigen which has oncogenic activity (such as oncogene-encoded products) it may be desirable to inactivate the oncogenic properties of the antigen while retaining its the immunogenic properties. This can be accomplished by mutagenesis techniques. For example, several oncogene encoded products are known to possess tyrosine kinase activity which is related in their transforming capabilities. Frame shift mutations, point mutations or DNA deletions within the tyrosine kinase domain of the oncogene can destroy tyrosine activity of the expressed product and render it devoid of tumorigenic activity. In cases where a tumorigenic region of the gene has not been identified, random mutations can be made within the gene and mutated genes can be selected for lack of oncogenic activity and retention of immunogenicity.

Cellular genes encoding tumor-associated antigens can be isolated from tumor cells employing standard techniques for isolation of genes. See e.g. Shih, C. and Weinberg, R. A. *Cell* 29 161–169 (1982). Many genes encoding tumor associated antigens have been cloned and thus are available for use in constructing the recombinant pox viruses of this invention. See e.g., Bargmann et al. (1986) *Nature* 319, 226–238 (neu gene); Martin-Zanca, D. et al., Cold Spring Harbor Symposia on Quantative Biology, V. LI, p. 985–992 (1986) (trk gene); Paxton, R. J. et al., *Proc. Natl. Acad. Sci. USA* 84; 920–924 (1987) (CEA).

2. Pox Viruses

Any member of the pox family can be used for the generation of recombinant viruses; for the purposes of vaccine development, the preferred pox virus is a virus which does not cause significant disease in normal humans or animals. For example, for humans and other mammals, the preferred pox virus is vaccinia virus, a relatively benign virus, which has been used for years as a vaccine against smallpox. Several strains of vaccinia, which differ in level of virulence, are available for use as vaccine strains; for the purposes of vaccination, a less virulent strain such as the New York State Board of Health Strain which still retains the ability to elicit an appropriate immune response is preferred. General techniques for integration of foreign DNA into vaccinia virus to produce a modified virus capable of expression foreign protein encoded by the foreign DNA are described by Paoletti et al. U.S. Pat. No. 4,603,112, the teachings of which are incorporated by reference herein.

3. DNA Vector for Recombination With Pox Virus

According to the method of this invention a foreign gene which encodes the cell-encoded tumor associated antigen is inserted into the genome of a pox virus so as to allow it to be expressed by the pox virus along with the expression of the normal complement of pox virus proteins (except for the pox viral protein encoded by the gene into which the foreign DNA is inserted). This is accomplished by first constructing a chimeric donor vector for recombination with pox virus which contains the DNA encoding the tumor associated antigen together with a pox viral promoter directing its expansion flanked by pox viral sequences. The flanking pox viral sequences can be any pox DNA region nonessential for replication; these allow the vector to recombine with pox virus in vivo at a specific region in the pox virus genome. This recombination results in integration of the DNA sequence encoding the tumor-associated antigen into the genome to produce a recombinant virus containing the DNA sequence;

The DNA vectors of this invention for integration of a DNA sequence of a cell-encoded tumor-associated antigen in expressible form into the pox viral genome contain the following elements:

a. a pox viral promoter linked to:

b. a DNA sequence containing a cloning site for insertion of DNA;

c. DNA sequences flanking the construct of elements a and b, the flanking sequences being homologous to a region of the pox viral genome which is nonessential to replication of the virus;

d. a replicon for vector replication in a prokaryotic host; and e. a gene encoding an assayable marker or indicator for selection of the vector in transformed prokaryotic hosts.

DNA vectors can also be constructed for insertion of two or more DNA sequences encoding different tumor associated antigens into pox virus. The antigen-encoding DNA sequences can be placed in tandem between the homologous flanking sequences, each sequence under the control of a separate pox viral promoter.

The cloning site generally comprises recognition sites for several restriction enzymes which allow different modes of insertion of DNA. An example sequence containing a multiple cloning site is: GGATCCCCGGGTACCGAGCTCGAATTC, which contains the recognition sequences and cleavage sites for the restriction endonuclease enzymes BamHI, SmaI, KpnI, SacI and EcoRI. Sequences containing additional or different recognition sites can be used. The cloning site is located adjacent to and downstream of a pox viral promoter such that an inserted gene can be placed under control of the promoter.

The pox viral promoter controls expression of the DNA sequence inserted at the cloning site and can be obtained from the species of pox virus with which the vector is designed to recombine.

The sequences flanking the construct of elements a and b (the pox viral promoter and adjacent cloning site) are homologous to a region of the pox viral genome which is not necessary for replication of the pox virus. Thus, recombination and integration of foreign DNA will occur at this site and the inserted DNA will not abolish viral replication. A preferred region for insertion into pox virus is within the gene coding for thymidine kinase (TK). Insertion into this region has several advantages: (1) the TK gene is not required for viral replication, so insertions into this gene do not abolish viral replication; (2) insertions into the TK gene do, however, partially inhibit viral replication, resulting in a recombinant pox virus that is less virulent and therefore possibly more suitable as a vaccine strain; and (3) it is possible to select recombinant viruses by selecting for insertional inactivation of the TK gene by selecting for insertional inactivation of the TK gene by growth in the presence of 5-bromodeoxyuridine. In order to obtain insertion into the TK gene, the recombination vector must contain flanking sequences homologous to the TK gene sequences.

Other nonessential regions of the pox virus genome can be used as flanking sequences to direct the stable integration of the DNA vector into the pox virus genome; these include, but are not limited to, regions of the genomic DNA contained on the HindIII and HindIIIF restriction fragments.

The replicon for replication in a prokaryotic host and the gene encoding the selectable indicator or marker allow the vector to be selected and amplified in a prokaryotic host such as E. coli to provide ample quantities of the vector DNA for eventual transfection of eukaryotic host cells for recombination. The replicon can be obtained from any conventional prokaryotic vector such as pBR322 or the pEMBL group of vectors. The selectable marker can be a gene conferring antibiotic resistance (e.g. ampicillin, chloramphenicol, kanamycin or tetracycline resistance).

Preferred vectors contain genetic elements which permit positive selection of recombinant viruses, i.e., those viruses which have recombined with the vector and, as a result, have acquired the sequence of interest. These elements for selection comprise a pox virus promoter, which controls expression of the indicator gene in the recombinant virus. The promoter and indicator gene (marker) are located between the flanking pox viral sequences so that the elements which allow for selection and the oncogene sequence of interest are co-integrated into the pox viral genome. Recombinant viruses can then be selected based upon expression of the marker or indicator.

A preferred gene for selection is the E. coli lacZ gene which encodes the selectable enzyme B-galactosidase. Methods of selection based upon expression of this enzyme are discussed below. Other selection methods include thymidine kinase selection as described above, and any drug resistance selection, for example, the selection that is provided by the gene encoding neomycin phospho-transferase, an enzyme which confers resistance to G418 (Franke et al., 1985. Mol. Cell. Biol. 5, 1918).

Alternatively, a negative type of selection can be employed. A preferred procedure of this type involves the use of a vaccinia virus such as vZ2 a recombinant derivative of the Wr vaccinia strain which contains a lacZ gene inserted within the HindIII F-region. Donor vectors containing homologous regions of the HindIIIF region and can recombine with vZ2 thereby replacing the lacZ gene with the DNA sequence encoding the tumor-associated antigen. Recombinant virus are lacZ⁻ and appear as white plaques in the presence of chromogenic substrate (e.g. Bluo-Gal™). See, Panicali, D. et al. (1986) Gene, 47:193–199.

As mentioned above, the preferred species of pox virus for insertion of DNA sequences for production of vaccines is the vaccinia species. Accordingly, preferred vectors are designed for recombination with the vaccinia virus and thus, the pox viral elements of the vector are derived from vaccinia virus. A vector for recombination with vaccinia virus can contain:

a. one or more vaccinia promoter (e.g. the vaccinia 11K, 7.5K, 30K, 40K or BamF promoter or modified versions of these promoters);

b. a multiple cloning site adjacent to each promoter;

c. a gene encoding a selectable marker (e.g. the E. coli lacZ gene) under control of a vaccinia promoter;

d. DNA sequences homologous to a region of vaccinia virus nonessential for replication of the virus, the DNA sequences flanking the construct of elements a–d (e.g., sequences of the vaccinia thymidine kinase gene);

e. a replicon for replication in a bacterial host; and f. a gene encoding a selectable marker under control of a prokaryotic promoter for selection of the vector in a prokaryotic host.

Vaccinia promoters are DNA sequences which direct messenger RNA synthesis from vaccinia genes during a vaccinia virus infection. Such promoters can be isolated from the vaccinia genome or can be constructed by DNA synthesis techniques. Promoters vary in strength of activity and in time of expression during the vaccinia virus life cycle; these parameters can be altered by mutation of the promoter sequence. The promoters can be isolated or synthesized to include or not include a translational initiation codon ATG as well as a multiple cloning site for convenient insertion of foreign gene in order to express these genes in vaccinia.

4. In Vivo Recombination

The intermediate DNA vectors containing the DNA encoding the tumor-associated antigen of interest (and the marker or indicator gene) flanked by appropriate pox viral sequences will undergo recombination with pox virus which results in integration of the flanked genes into the pox viral genome. This recombination will occur in a eukaryotic host cell. Appropriate host cells for recombination are cells which are 1) infectable by pox virus and 2) transfectable by the DNA vector. Examples of such cells are chick embryo fibroblast, CV-1 cells (monkey kidney cells), HuTK-143 cells (human cells), and BSC40 (monkey) cells.

The cells are first infected with pox virus and then transfected with the intermediate DNA vector. Viral infection is accomplished by standard techniques for infection of eukaryotic cells with pox virus. See e.g., Paoletti et al., supra. The cells can be transfected with the intermediate DNA vector by any of the conventional techniques of transfection. These include the techniques of calcium phosphate precipitation, DEAE dextran, electroporation and protoplast fusion. The preferred technique is the calcium phosphate precipitation technique.

After infection and subsequent transfection, the cells are incubated under standard conditions and virus is allowed to replicate during which time in vivo recombination occurs between the homologous pox virus sequences in the intermediate vector and the pox virus sequences in the genome.

Recombinant viral progeny are then selected by any of several techniques. The presence of integrated foreign DNA can be detected by hybridization with a labeled DNA probe specific for the inserted DNA encoding the tumor antigen. Alternatively, virus harboring the tumor cell sequence can be selected on the basis of inactivation of the viral gene into which the foreign DNA was inserted. For example, if the DNA vector is designed for insertion into the thymidine kinase (TK) gene of a pox virus, viruses containing integrated DNA will be unable to express thymidine kinase (TK$^-$) and can be selected on the basis of this phenotype. Preferred techniques for selection are based upon co-integration of a gene encoding a marker or indicator gene along with the gene of interest, as described above. A preferred indicator gene is the *E. coli* lacZ gene which encodes the enzyme B-galactosidase. Selection of recombinant viruses expressing B-galactosidase can be done by employing a chromogenic substrate for the enzyme. For example, recombinant viruses are detected as blue plaques in the presence of the substrate 5-bromo-4-chloro-3-indolyl-B-D-galactoside or other halogenated-indolyl-B-D-galactosides (BluoGal™).

Another preferred technique involves the use of virus vZ2 as described above.

Recombinant viruses which express the inserted DNA sequence encoding the tumor associated antigen can be determined by any of several standard procedures including RNA dot blots, black plaque assays, immunoprecipitation (employing antibody reactive with the antigen), etc.

5. Vaccines

Live recombinant viruses expressing an an immunogenic a cell encoded tumor associated antigen can be used to induce an immune response against tumor cells which express the protein. These recombinant viruses may be administered intradermally, as was conventionally done for small pox vaccination, or by other routes appropriate to the recombinant virus used. These may include among others, intramuscular, subcutaneous, and oral routes. Vaccination of a host organism with live recombinant vaccinia virus is followed by replication of the virus within the host. During replication, the oncogene sequence is expressed along with the normal complement of vaccinia genes. If the oncogene product is an antigen, it will stimulate the host to mount an immunological response, both humoral and cell-mediated, to the tumor associated antigen (as well as to vaccinia virus itself).

6. Use of Recombinant Pox Viruses to Produce Therapeutic and Diagnostic Reagents Recombinant pox virus which express tumor-associated antigens can also provide a means to produce antibody against the antigen for use therapeutics or diagnostics. Infection of experimental animals with the recombinant pox viruses can be used to raise both monoclonal antibodies and polyclonal antisera which recognize the tumor associated antigen. The antibodies may be useful in passive immunotherapy against tumor. In diagnostics, these monoclonal and/or polyclonal antibodies can be used as capture antibody for immunoassay in the RIA or ELISA format, to detect the presence or to quantify the antigen in a biological fluid (e.g., urine, blood, etc.)

Alternatively, cells infected in vitro with the recombinant pox viruses can be used as a source of the tumor associated antigens. Compatible host cells are infected with a recombinant pox virus capable of expressing the desired tumor associated antigen and cultured under conditions which allow the virus to replicate and express the antigen. The antigen is then isolated from the cells.

The invention is illustrated further by the following exemplification.

EXEMPLIFICATION

Virus and Cells

CV-1 cells were obtained from the American Type Culture Collection (ATCC#CCL70) and were grown in Minimal Essential Media (MEM) supplemented with 10% fetal calf serum. Vaccinia virus strain VZ2 is a derivative of the WR strain which contains the lacZ gene inserted at the Bam HI-site in the vaccinia virus Hind III F-region. Panicali, D., Grzelezcki, A. & Long, C. (1986) Gene 47, 193–199.

Construction of a Chimeric Donor Plasmid for in Vivo Recombination

PEVAC is a recombinant plasmid which contains a 2.5 kb Pst I fragment corresponding to the middle portion of the vaccinia virus HindIII F-fragment. Panicali, D., Davis, S. W., Mercer, S. R. & Paoletti, E. (1981). *J. Virol.* 37, 1000–1010; this PstI-fragment is inserted into the PstI site of a derivative of pEMBL18 (Dente, L., Cesareni, G. & Cortese, R. (1983) *Nucleic Acids Res.* 11, 1645–1655), lacking a BamHI restriction site. Adjacent to the BamHI site in the vaccinia virus fragment is an early vaccinia promoter which has been used previously to express a variety of antigens. Panicali, D., Davis, S. W., Weinberg, R. A. & Paoletti, E. (1983) *Proc. Natl. Acad. Sci. USA* 80, 5364–5368. This vector was used to insert the rat neu cDNA described by Bargmann et.al., (1986) *Nature* 319, 226–230. In order to disable the oncogenic function of the neu-encoded protein, an internal deletion was made in the neu cDNA clone by deleting the sequences between the Bam HI site at nt 2175 and the Bg1II site at nt 3250 of the neu cDNA sequence. Bargmann, C. I. Hung, M. C. & Weinberg, R. A. (1986) *Nature* 319, 226–230. This deletion removes the region that specifies the tyrosine kinase domain of the neu-encoded protein. In addition it generates a frame-shift mutation downstream of the kinase domain, creating a new stop codon shortly after the Bg1II site at nt 3250. The resulting construct was designated pEVAC-neu. (FIG. 1 shows a schematic representation of the construction of the pEVAC-neu plasmid; at the top a schematic representation of the p185 gene is shown; TM indicates the position of the transmembrane domain and the black box indicates the domain with homology to proteins with tyrosine kinase activity). The pEVAC-neu plasmid has been placed on deposit at the American Type Culture Collection, Rockville, Maryland and assigned the accession number.

Construction, Identification and Purification of Recombinant Vaccinia Virus

Recombinant vaccinia virus was constructed as previously described. See Panicali, D. & Paoletti, E. (1982) *Proc. Natl. Acad. Sci. USA* 79 4927–4931. In short, CV-1 cells (10 cells per 6 cm plate) were infected with vaccinia virus VZ2 at a multiplicity of infection of 2 and incubated for 40 minutes at 37° C. Cells were then transfected with 27 ug of calcium orthophosphate precipitated pEVAC-neu DNA. After a further incubation for 16 hours at 37° C. virus was harvested and titered.

The DNA used for this transfection was able to recombine with homologous sequences in the HindIII F-region of the VZ2 genome, thereby replacing the lac-Z gene. As a result, recombinant virus appeared as white plaques in the presence of Bluo-Gal (Bethesda Research Laboratories), while the parental virus VZ2 appeared blue. White plaques were picked and five rounds of plaque purification were performed. One of the recombinant viruses, designated ABT9-4, had a final concentration of $1.14 \times 10^{13}$ pfu/ml.

ELISA Assay

Serum antibody responses to vaccinia were detected using a solid-phase ELISA. Sucrose-gradient purified vaccinia virus (WR strain) at a protein concentration of 10 ug/ml in 0.05M carbonate buffer pH9.6 was used to passively coat microtiter wells. After 2 hours at 37° C., the solution was aspirated and dilutions of test sera were added to the wells. Following a 1 hour incubation at 37° C., the wells were washed three times with PBS supplemented with 0.05% Tween 20 and were then incubated with HRP-labeled goat anti-mouse IgG (Jackson Immunoresearch) at a dilution of 1:5000. Rat sera were tested using an HRP-labeled F(Ab)$_2$ goat anti-rat IgG, also at a dilution of 1:5000. After incubation with the second antibody, the wells were again washed three times with PBS-Tween, and color was developed using 3,3,5,5'-tetramethyl-benzidine (TMB, Sigma). 10 mg of TMB was dissolved in 1 ml of dimethylsulfoxide (DMSO and 100 ul of this solution was added to 5 ml of acetate citrate buffer pH 6.0 along with 10 ul of 3% H$_2$O$_2$. Color was allowed to develop for five minutes, after which the reaction was stopped by the addition of 2.5M H$_2$SO$_4$. The absorbance was read at 450 nm on a Dynatech MinireaderII plate reader. Serum antibody responses to the rat p185 protein were determined similarly, using a cell lysate of DHFR G8 cells to coat the microtiter wells. DHFR G8 cells over-express the non-transforming rat p185 protein. See Hung, M. C., Schechter, A. L., Chevray, P. Y., Stern, D. F. & Weinberg, R. A. (1986) *Proc. Natl Acad. Sci. USA* 83, 261–264. ELISA titers against the p185 protein are reported as the last dilution which still gives as OD of at least 0.05 units greater than the OD seen for background binding. ELISA titers against vaccinia virus are defined as the dilution of serum which gives an O.D. which is half the maximum O.D. obtained in the assay.

Results

Construction of a NEU-Containing Recombinant Vaccinia Virus

The neu oncogene was initially detected by transfection of DNA from chemically induced rat neuroblastomas into NIH3T3 mouse cells. Padhy, L. C., Shih, C., Cowing, D. C., Finkelstein, R. & Weinberg, R. A. (1982) *Cell* 28; 865–871, Shih, C., Padhy, L. C., Murray, M. & Weinberg, R. A. (1981) *Nature* 290, 261–263. The resulting transfectants were found to be tumorigenic in NFS mice. These mice also were found to mount a strong humoral immune response against the extracellular portion of the p185 specified by the transfected rat gene. Padhy, L. C., Shih, C., Cowing, D. C., Finkelstein, R. & Weinberg, R. A. (1982) *Cell* 28, 865–871. This p185 protein has many properties of a growth factor receptor. In addition to the extracellular domain, it has a transmembrane domain and an intracellular domain with sequences that share homology with proteins having tyrosine kinase activity. Bargmann, C. I., Hung, M. C. & Weinberg, R. A. & Paoletti, E. (1983) *Proc. Natl. Acad. Sci. USA* 80, 5364–5368; Schechter, A. L., Hung, M. C., Vaidyanathan, L., Weinberg, R. A., Yang-Feng, T. L., France, U., Ullrich, A. and Coussens, L. (1985) *Science* 229, 976–978. The neu-encoded protein found in the oncogene-transfected cells differs from its normal counterpart by a single amino acid substitution in the transmembrane domain of the protein, Bargmann, C. I., Hung, M. C. and Weinberg, R. A. (1986). *Cell* 45, 649–657.

We adapted a cDNA clone of the neu oncogene for introduction into the vaccinia vector. We first removed the bulk of the sequences specifying the cytoplasmic domain of the protein. By deleting the kinase domain, we fully disable the oncogenic effector functions of p185 while leaving intact the immunogenic ectodomain. The truncated neu cDNA clone, encoding the ectodomain, the transmembrane anchor domain, and approximately 50 amino acid residues of the intracellular domain, was then joined with the Bam-F promoter of vaccinia virus. The resulting construct was designated pEVAC-neu. This gene was then introduced into vaccinia virus by homologous recombination (Materials and Methods). The resulting chimeric virus was termed ABT 9-4.

Expression in Infected Cells

Figure 2:
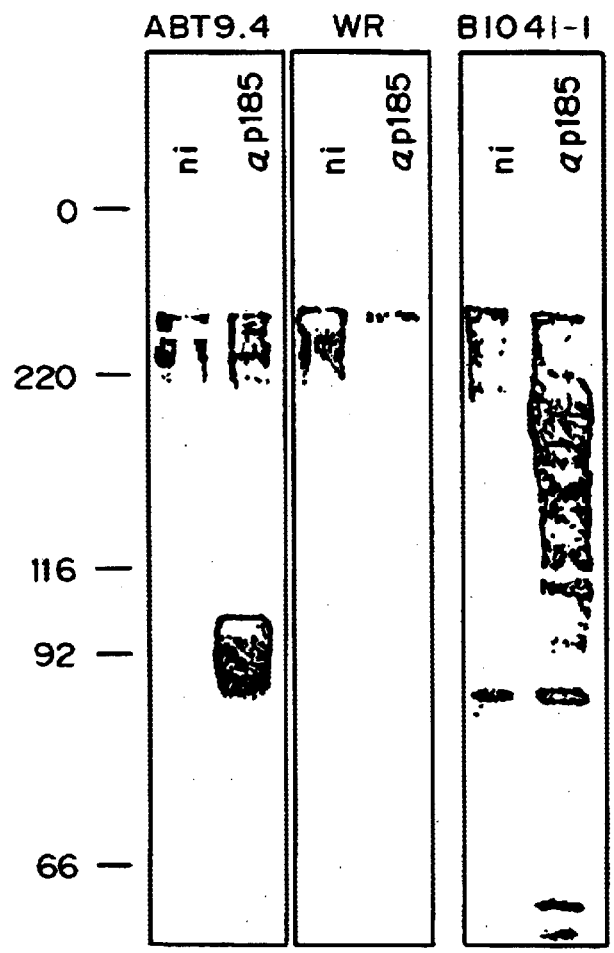
FIG. 2 shows the expression of the internally deleted p185 in vaccinia virus-infected cells.

To test whether the manipulated neu gene encoded by the recombinant vaccinia virus is expressed in infected cells, CV-1 cells were infected at a multiplicity of infection of 10 pfu per cell with either the ABT 9-4 recombinant virus or an equal dose of WR wild-type vaccinia virus. Directly after infection, $^{35}$S-cysteine was added and infection was allowed to proceed for 6 hours. Following this, infected cells were lysed with RIPA buffer and lysates were immunoprecipitated with the anti-p185 monoclonal antibody 7.16.4 (Drebin, J. A. et al. (1984) *Nature* 312 545–548). This antibody reacts with a still undefined determinant located in the ectodomain of the protein. FIG. 2 shows SDS polyacrylamide gel electrophoresis of the proteins immunoprecipitated with anti-p185 monoclonal antibody (Lanes indicated "ni" represent lysates precipitated with a non-immune mouse serum; lanes indicated "p185" were immunoprecipitated with the 7.16.4 monoclonal antibody; a lysate from B101-1-1 cells (expressing the transforming p185 protein) was added as a control. The positions of the molecular weight markers are indicated.) As can be seen in FIG. 2, ABT 9-4-infected cells, but not wild-type vaccinia virus-infected cells, produce a 100 kD protein that is precipitated by the monoclonal antibody 7.16.4. The molecular weight of the precipitated protein is in good agreement with that calculated for the protein specified by the truncated neu gene. We conclude from these experiments that the ABT 9-4 recombinant directs the synthesis of a truncated p185 molecule.

Immune Reactivity in Virus-Infected Mice

The ability of inbred mice to respond to a foreign antigen is known to differ widely between strains. Accordingly, we first tested various mouse strains for their ability to mount an immune response against the rat p185 protein. To do this, four-week old mice of various strains were inoculated intraperitoneally with $10^8$ pfu of either wild-type vaccinia virus or an equal dose of ABT9-4 recombinant virus. After 4 weeks, a booster injection of $10^8$ pfu of virus was given. Sera were collected two weeks later. The production of antibodies directed against the neu oncogene product was followed using an ELISA assay (Materials and Methods). The results, shown in Table 1, demonstrate that not all mouse strains have the ability respond to the rat p185 protein. We assume that these differences are due to differences in MHC haplotypes of these mouse strains. For example, we note that both mouse strains of the $H-2^d$ haplotype did not respond to the neu product. In subsequent experiments we concentrated on the use of NFS mice as a model. These mice are closely related to the strain from which the NIH3T3 cell line arose. They thus represent a reasonable host for oncogene-transformed NIH3T3 tumor cells.

TABLE 1

Antibody titers of different mouse strains to the rat p185 protein following vaccination with vaccinia recombinant ABT9-4.

| Strain | Haplotype | Sera | ELISA Titer |
| --- | --- | --- | --- |
| Balb/c | $H-2^d$ | non-immune | 0 |
| | | immune | 0 |
| C3H/HeN | $H-2^k$ | non-immune | 0 |
| | | immune | 1:80 |
| DBA/2N | $H-2^d$ | non-immune | 0 |
| | | immune | 0 |
| NFS | outbred | non-immune | 0 |
| | | immune | 1:40 |
| NZW/LacJ | $H-2^z$ | non-immune | 0 |
| | | immune | 1:80 |
| SM/J | $H-2^v$ | non-immune | 0 |
| | | immune | 0 |
| Swiss | outbred | non-immune | 0 |
| | | immune | 1:80 |

Mice were immunized intraperitoneally with $10^8$ pfu of ABT9-4 recombinant virus. After four weeks mice were boosted with a similar dose of virus. Titers indicated were obtained with sera collected two weeks after the boost. ELISA assays were performed as described in Materials and Methods.

Figure 3:
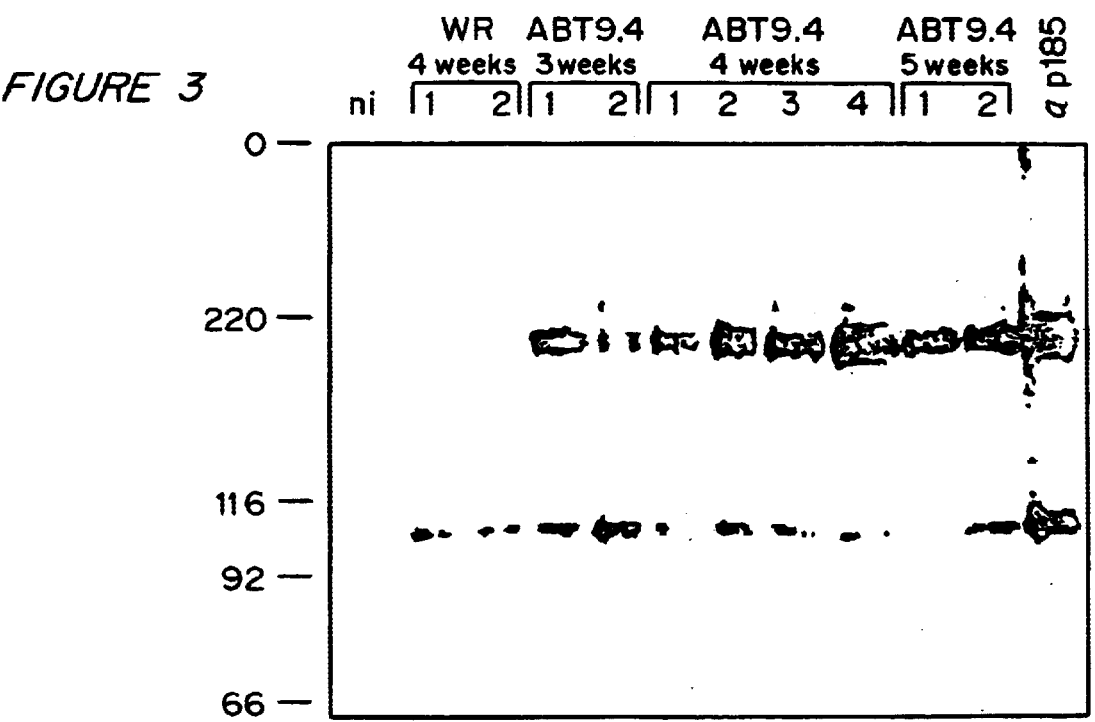
FIG. 3 shows the development of antibody response to p185 in vaccinia virus-infected mice.

We next determined the kinetics of the development of immunity against the p185 protein in NFS mice immunized with the vaccinia virus recombinant. To do this, NFS mice were immunized with a single subcutaneous injection of $10^8$ pfu of the ABT9-4 recombinant virus. Control mice were immunized in parallel with an equal dose of wild type vaccinia virus. To monitor the development of immunity, mice were bled at weekly intervals and the sera were tested for an ability to precipitate p185 from lysates of 32p labeled DHFR G8 cells. FIG. 3 shows SDS acrylamide gel electrophoresis as follows: Lane 1: non-immune mouse serum; lanes 2 and 3: sera from mice immunized with wild type vaccinia virus collected 4 weeks post immunization; Lanes 4 and 5: sera from mice immunized with ABT9-4 recombinant virus, 3 weeks post immunization; Lanes 6–9: sera from ABT9-4 immunized mice collected 4 weeks post immunization; Lanes 10 and 11: Sera from ABR9-4 immunized mice, 5 weeks post immunization; Lane 12: monoclonal antibody 7.16.4.

As can be seen in FIG. 3, infection by the recombinant vaccinia virus led to the development of high titer antisera against p185 within a period of three weeks. The serum titers showed a further slight increase in the next week. A similar pattern was found for the development of immunity against vaccinia virus in these mice as measured in an ELISA assay (data not shown). As expected, no reactivity against p185 was developed when mice were exposed to the wild-type vaccinia virus (FIG. 3, lanes 2 and 3). These data made it clear that a single injection of recombinant vaccinia virus leads to the efficient-induction of anti-p185 antibody within a period of 4 weeks.

Tumor Rejection in Immune Mice

Subsequent experiments were designed to test whether immunization of NFS mice with the ABT9-4 recombinant virus had an effect on the tumorigenicity of NIH3T3 cells transformed by the neu oncogene. These NIH3T3 derivatives, termed B104–101, carry the rat neu oncogene and display substantial amounts of oncogene-encoded p185 on their surface, Padhy, L. C., Shih, C., Cowing, D. C., Finkelstein, R. & Weinberg, R. A. (1982) Cell 28, 865–871.

Young adult NFS mice were injected intraperitoneally with $10^8$ pfu of wild-type or recombinant vaccinia virus and challenged with various doses of B104-1-1 tumor cells four weeks post immunization. Both viruses provoked similar anti-vaccinia virus immune response in these mice, as measured in a vaccinia virus ELISA assay (data not shown). The growth of tumors at the site of injection was followed in time and is presented in FIG. 4. Young adult NFS mice were immunized with a single injection of $10^8$ pfu of wild type vaccinia virus or ABT9-4 recombinant virus. Four weeks later, these mice were challenged with either $2 \times 10^6$ (panel A) or $1 \times 10^7$ neu-transformed NIH3T3 cells (panel B). As a control, a group of immunized mice was challenged with Ha-ras transformed NIH3T3 cells (panel C). Each group of consisted of 10 mice, the data are represented as the average tumor area±SD. (●): Wild type vaccinia immunized mice, (□) ABT9-4 recombinant immunized mice.

The data show that in wild-type virus-infected animals, B104-1-1 cells grow progressively for the first 12 to 19 days, after which the tumors begin to regress spontaneously and finally disappear completely after about 5 weeks. A similar pattern of tumor growth and rejection was observed when non-immunized NFS mice were injected with an equal dose of B104-1-1 cells (data not shown). Since tumor regression is not seen when these cells are injected in athymic nude mice, it is most likely tumor regression is caused by the spontaneous development of immunity against these cells.

Figure 4C:
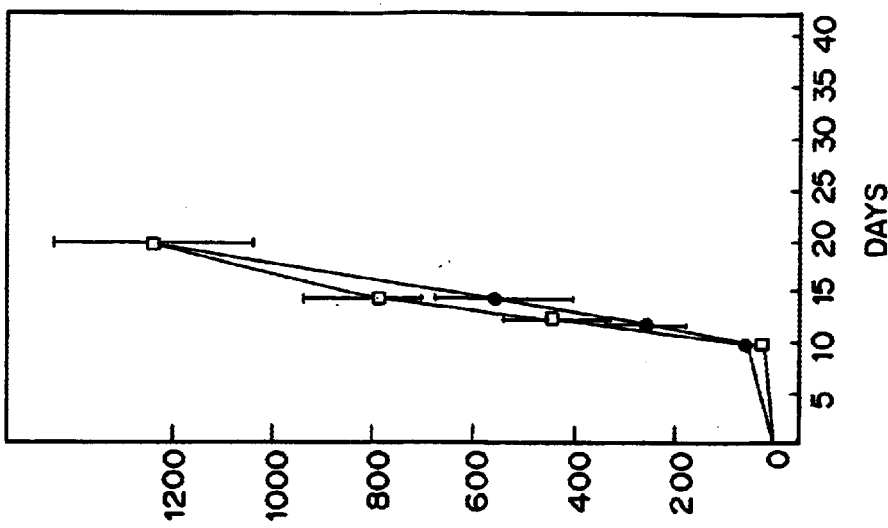
FIG. 4 shows the results of tumor challenge of mice vaccinated with vaccinia virus recombinants.
Figure 4B:
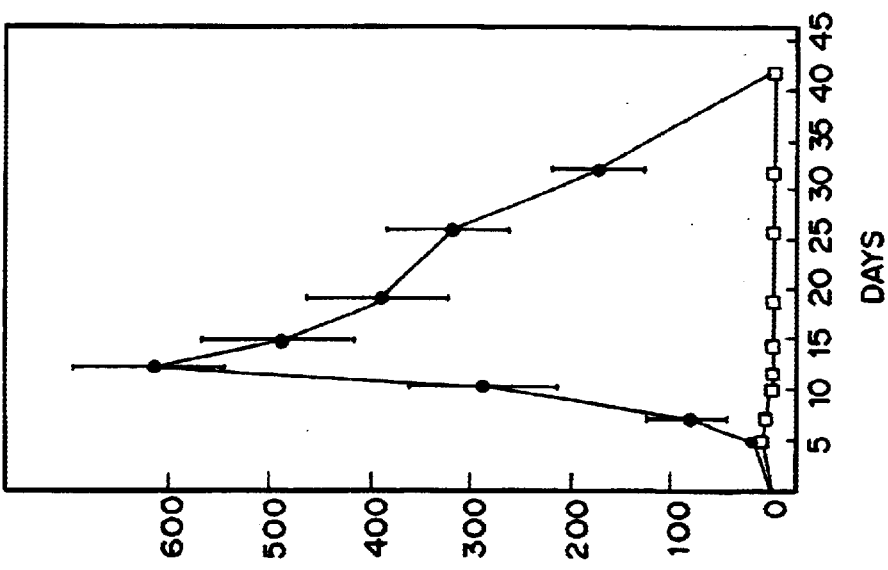
Figure 4A:
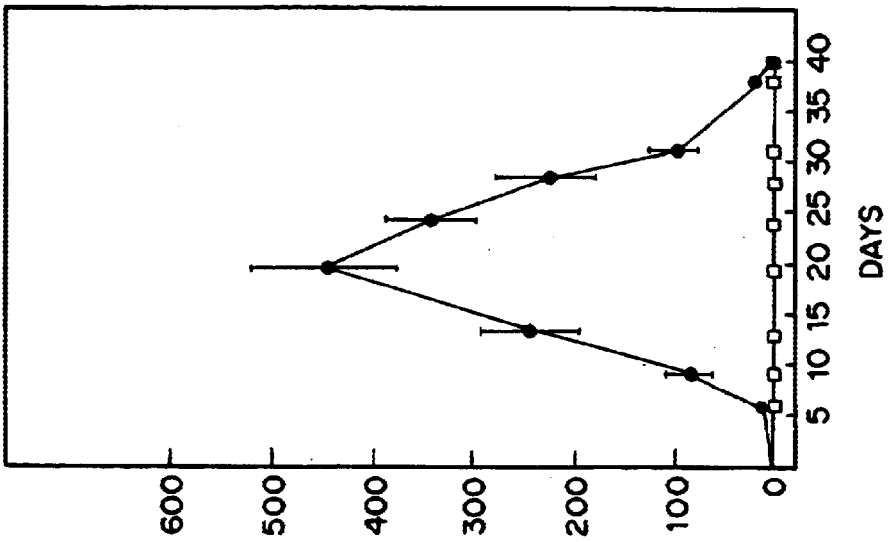

A quite different result was obtained when B104-1-1 cells were injected into NFS mice immunized with the ABT9-4 recombinant virus (FIGS. 4A, B). Following injection of a tumor cell dose of $2 \times 10^6$ cells per animal, no tumor developed at the site of injection; at a dose of $10^7$ cells per animal, a small nodule developed at the site of injection within five days which quickly disappeared in the next several days. These results show that immunization with the vaccinia virus recombinant drastically inhibits the outgrowth of p185-expressing tumor cells.

No difference in tumor outgrowth was seen when both wild-type virus immunized mice and recombinant virus-immunized mice were challenged with Ha-ras-transformed NIH 3T3 cells. This showed that the immune protection brought about by the recombinant vaccinia virus is specific for tumor cells displaying the neu oncogene-encoded p185 (FIG. 4, panel c).

Immune Reactivity in Rats

The introduction of the neu-transformed NIH3T3 cells into NFS mice represents an experimental artifice in that these tumor cells present an immunogenic rat protein to the mouse host. The immunogenicity of this protein appears to induce the eventual rejection of tumors formed from these cells (FIGS. 4A, B). This situation would seem to contrast with one arising in an animal bearing an autochtonous tumor or a tumor deriving from fully syngeneic cells. In these latter cases, no antigen of allogeneic origin is presented, and potently immunogenic proteins are usually not displayed by the tumor cells.

This reasoning caused us to question whether immunity to p185 and associated tumor rejection could be developed in a fully syngeneic system. Thus we attempted to immunize BDIX rats with the vaccinia-induced p185 antigen. The neuroblastomas in which the neu oncogene arose were induced in rats of this strain. Schubert, D., Heinemann, S., Carlisle, W., Tarikas, H., Kimes, B., Patrick, J., Steinbach, J. H., Culp, W. & Brandt, B. L. (1974). *Nature* 249, 224–227. Though the ectodomain encoded by the vector-borne neu gene is identical to that of the normal p185 expressed in the BDIX rat, the possibility remained that the amino acid substitution present in the transmembrane domain of the oncogene-encoded protein might confer immunogenicity on this protein. This amino acid substitution is specified by the truncated neu gene borne by the vaccinia vector.

To measure the effectiveness of the vaccinia recombinant virus in rats we immunized the following rat strains with the ABT9-4 recombinant: BDIX, Fisher, Lewis, Sprague Dawley, Wistar-Kyoto. Weanling rats were immunized by intraperitoneal injection of $10^8$pfu of wild-type vaccinia virus or ABT9-4 recombinant virus followed by a second intraperitoneal injection of $10^8$pfu of virus three weeks later. Two weeks after the booster injection, animals were bled and their sera were tested for reactivity with vaccinia virus antigens. Both strains of virus grew well in these rats, equivalent anti-vaccinia serum response (titers 1:10,000) in an vaccinia virus ELISA were found in all rat strains). These sera were also tested for an ability to precipitate either the normal or the transforming version of the p185 protein from lysates of neu-transfected cells. No reactivity against either protein was found in any of the rat sera tested (data not shown).

Although no humoral immunity against p185 was elicited in these rats, it remained possible that these rats would display an effective anti-tumor response. Accordingly, we tested whether immunization of BDIX rats by the ABT9-4 virus would result in inhibition of the growth of B104 neuroblastoma cells. These B104 cells derived directly from a chemically-induced tumor of a BDIX rat and express the transforming version of p185. Schubert, D., Heinemann, S., Carlisle, W., Tarikas, H., Kimes, B., Patrick, J., Steinbach, J. H., Culp, W. & Brandt, B. L. (1974) Nature 249, 224–227. Exposure of the BDIX rats to the ABT 9-4 virus led to no significant inhibitory effect on the growth of injected B104 tumor cells (data not shown). It appears that the ectodomain of the neu-p185 that is expressed in vaccinia vector-infected cells is not immunogenic in BDIX rats, in that neither anti-p185 serum response nor anti-tumor immunity was observed. It remains possible however that recombinants that express the neu-encoded p185 protein at a higher level, possibly used in combination with drugs that reduce tolerance of animals against a self product, may be more effective in inducing immunity in syngeneic animals. At present it appears however that the presence of an amino acid substitution in the transmembrane domain of the p185 protein is not sufficient to overcome a tolerance which the rat immune system shows towards this protein.

We describe the construction of a vaccinia virus recombinant expressing the extracellular domain of the rat neu oncogene and its use in tumor immunotherapy. Our data indicate that the recombinant vaccinia virus-induced immunity results in the full protection of mice from subsequent tumor challenge with cells that express the rat neu-oncogene. The fact that the subtle differences between rat and mouse neu proteins were sufficient to induce a potent immune response against the rat protein in immunized mice suggests that recombinant pox viruses will be powerful tools for the induction of immunity against tumor cells whose antigenicity in many cases does not differ greatly from the cells from which the tumor arose.

The immunological effector mechanisms that are involved in inducing anti-tumor immunity have not been studied extensively. Our data indicate that the vaccinia virus recombinant can induce significant antibody titers against the rat neu oncogene protein in vaccinated mice. In the present study complete protection against tumor challenge with neu-transformed cells was observed, suggesting that immune mechanisms other than humoral immunity were induced by the vaccinia virus recombinant. In support of this view in the finding of others who have shown that vaccinia virus vectors can effectively induce T-cell mediated immune responses in immunized animals. Earl, P. L., et al. (1986) *Science* 234, 728–731. However, inhibition of tumorigenicity in these experiments was only partial, indicating that antibody treatment alone is not sufficient to cause complete regression of the tumor induced by the neu-transformed cells. In the present study complete protection against tumor challenge with neu-transformed cells was observed, suggesting that immune mechanisms other than humoral immunity was induced by the vaccinia virus recombinant. In support of this view is the finding of others who have shown that vaccinia virus vectors can effectively induce T-cell mediated immune responses in immunized animals.

Our data demonstrate that immunization with a single, well-defined antigen can confer protection against tumor cells bearing this antigen. This is to be contrasted with other experimental models in which animals are immunized with tumor cells or tumor cell extracts in which a complex mixture of antigens may act to provoke immunity.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A recombinant pox virus, comprising a DNA sequence encoding a cell-encoded tumor-associated antigen, wherein the cell-encoded tumor antigen is encoded by the neu gene, the ros gene, the trk gene, the kit gene or an immunogenic portion thereof, and wherein expression of said cell-encoded tumor-associated antigen in an animal infected with said pox virus results in generation on an immune response to said antigen by said animal.

2. A recombinant pox, virus comprising a DNA sequence encoding a cell-encoded tumor-associated antigen, wherein the cell-encoded tumor-associated antigen is a growth factor receptor or growth factor receptor-like cell surface molecule, wherein expression of said cell encoded tumor-associated antigen in an animal infected with said pox virus results in generation on an immune response to said antigen by said animal.

3. A The recombinant pox virus of claim 2, wherein the receptor or receptor-like surface molecule is encoded by the c-erbB gene.

4. A vector for insertion of DNA encoding a cell-encoded tumor-associated antigen pox virus comprising a DNA sequence encoding a cell-encoded tumor-associated antigen comprising a. a prokaryotic origin replication;
b. a pox viral promoter;
c. a DNA sequence encoding the cell-encoded tumor-associated antigen under the direction of the pox viral promoter wherein the DNA sequences for the cell-encoded tumor-associated antigen are selected from the group consisting of the neu gene, the ros gene, the trk gene, the kit gene the c-erbB gene and a DNA sequence encoding an immunogenic portion thereof; and
d. DNA sequences homologous to a region of the pox virus genome where the DNA sequence encoding the cell-encoded tumor-associated antigen is to be inserted, the DNA sequences flanking the construct of element c.

5. A recombinant pox virus comprising a DNA sequence encoding a cell-encoded tumor-associated antigen, wherein the cell encoded tumor-associated antigen is carcinoembryonic antigen or CA-125, wherein expression of said cell encoded tumor-associated antigen in an animal infected with said pox virus results in generation on an immune response to said antigen by said animal.

6. A vector for insertion of DNA encoding a cell-encoded tumor-associated antigen pox virus comprising a DNA sequence encoding a cell-encoded tumor-associated antigen comprising a. a prokaryotic origin replication;
b. a pox viral promoter;
c. a DNA sequence encoding the cell-encoded tumor-associated antigen under the direction of the POX viral promoter wherein the cell-encoded tumor associated antigen is carcinoembryonic antigen or CA-125; and
d. DNA sequences homologous to a region of the pox virus genome where the DNA sequence encoding the cell-encoded tumor-associated antigen is to be inserted, the DNA sequences flanking the construct of element c.

7. A recombinant pox virus comprising a DNA sequence encoding a cell-encoded tumor-associated antigen, wherein the cell encoded tumor-associated antigen is a human oncogene or proto-oncogene, wherein expression of said cell encoded tumor-associated antigen in an animal infected with said pox virus results in generation on an immune response to said antigen by said animal, and wherein said oncogene or proto-oncogene is not a carcinoembryonic antigen, CA-125 or melanoma associated antigen.

* * * * *